United States Patent
Lapanashvili et al.

(10) Patent No.: US 9,498,629 B2
(45) Date of Patent: Nov. 22, 2016

(54) METHOD AND DEVICE FOR COUNTERPULSATION THERAPY

(71) Applicant: MARJI LTD., Tbilisi (GE)

(72) Inventors: Leri Lapanashvili, Tbilisi (GE); Dmitry Ivanovich Minaev, Moscow (RU); Vladislav Evgenevich Kuzmin, Moscow (RU); Mikhael Alexandrovich Bajin, Moscow (RU)

(73) Assignee: MARJI LD., Tbilisi (GE)

( * ) Notice: Subject to any disclaimer, the term of this patent is extended or adjusted under 35 U.S.C. 154(b) by 185 days.

(21) Appl. No.: 14/347,473

(22) PCT Filed: Sep. 25, 2012

(86) PCT No.: PCT/GE2012/000003
§ 371 (c)(1),
(2) Date: Mar. 26, 2014

(87) PCT Pub. No.: WO2013/045957
PCT Pub. Date: Apr. 4, 2013

(65) Prior Publication Data
US 2014/0249593 A1    Sep. 4, 2014

(30) Foreign Application Priority Data

Sep. 26, 2011    (GE) .................. 2011 0 12395

(51) Int. Cl.
*A61N 1/365*    (2006.01)
*A61N 1/36*    (2006.01)

(52) U.S. Cl.
CPC ....... *A61N 1/36585* (2013.01); *A61N 1/36017* (2013.01); *A61N 1/36042* (2013.01); *A61N 1/36514* (2013.01)

(58) Field of Classification Search
CPC ...... A61N 1/36003; A61N 1/05; A61N 1/36; A61N 1/3962; A61N 1/3956; A61N 1/3601; A61N 1/36021; A61N 1/36585; A61M 5/14276; A61M 2001/122; A61M 1/1086; A61B 5/0205; A61B 17/1327; A61B 17/135; A61H 1/02059; A61H 31/006
USPC .............. 607/48, 115–116, 2–5, 42, 46; 600/16–17, 483; 601/34, 41; 606/202–203
See application file for complete search history.

(56) References Cited

U.S. PATENT DOCUMENTS 5,014,700 A * 5/1991 Alt .................. A61N 1/36585
                                                  607/18
5,645,575 A * 7/1997 Stangl ............. A61N 1/36585
                                                  607/17

(Continued)

FOREIGN PATENT DOCUMENTS

GE        118      12/1994
GE        366       7/1996

(Continued)

OTHER PUBLICATIONS

International Search Report for International Application No. PCT/GE2012/000003 mailed Jul. 4, 2013 (5 pages).

(Continued)

*Primary Examiner* — Christopher D Koharski
*Assistant Examiner* — Roland Dinga
(74) *Attorney, Agent, or Firm* — Merchant & Gould P.C.

(57) ABSTRACT

A method of counterpulsation therapy is provided, the method comprising use of a combination of cardiac electrical activity and acoustic signals in such a manner that initially R wave on a cardiogram and then II (aortic) sound are determined, and, after the II sound has been determined, stimulation of muscles by means of electric impulses is initiated. A device for performing the above described method comprises a sensor of the signal of cardiac electrical activity and a sensor of cardiac acoustic signal; a unit for blocking the cardiac electrical activity signal; a unit for blocking the acoustic signal; and a control device coupled with muscle stimulating devices.

3 Claims, 3 Drawing Sheets

(56) References Cited

U.S. PATENT DOCUMENTS

2003/0233118 A1 12/2003 Hui
2009/0036938 A1 2/2009 Shipley et al.

FOREIGN PATENT DOCUMENTS

| | | |
|---|---|---|
| RU | 2 071 368 | 1/1997 |
| SU | 936931 | 6/1982 |
| WO | WO 01/13990 | 3/2001 |
| WO | WO 2009/017722 | 2/2009 |

OTHER PUBLICATIONS

Written Opinion for International Application No. PCT/GE2012/000003 (6 pages).

* cited by examiner

METHOD AND DEVICE FOR COUNTERPULSATION THERAPY

This application is a National Stage Application of PCT/GE2012/000003, filed 25Sep. 2012, which claims benefit of Serial No. AP 2011 0 12395, filed 26 Sep. 2001 in Georgia and which applications are incorporated herein by reference. To the extent appropriate, a claim of priority is made to each of the above disclosed applications.

BACKGROUND

The present invention pertains to the medical field, and more particularly to a method and apparatus for counterpulsation therapy that can be used in treatment of cardiovascular disorders and in regenerative medicine as well.

Known in the art is a method of external aortal counterpulsation (Patent of Georgia GE 118), comprising transposing the skeletal muscle graft into a thoracic cavity and fixing it onto the aorta, and electric stimulation of the graft by means of electrodes in counterpulsation mode.

Also known is a method of non-invasive electric stimulation of a muscle (patent of Georgia GE 366) comprising affixing electrodes to the selected muscle, preliminarily determining cardiac rhythm and impacting by above-threshold electric pulses synchronized with the cardiac rhythm.

The mentioned method provides for the use of a cardioscope to choose the moment of the cardiac cycle in which the electrical impact has to be occurred, mostly in the counterpulsation mode (in diastole phase).

The problem related to the use of the above mentioned methods is that it is necessary to clearly identify T wave on an electrocardiogram tracing for the purposes of initiating the stimulation in diastole phase, because a time delay equal to Q-T interval needs to be defined by an operator.

To this end, the operator has to displace the electrodes of a single-channel sensor until the clear contours of R and T waves in an electrocardiogram tracing has been reached, or to use a 12-channel ECG device. Thereby the procedure becomes inconvenient and time-consuming.

In using the above mentioned methods, the stimulation may start in a wrong phase since the physiological deviation of the cardiac rhythm normally occurs (even in healthy humans), that is expressed in a cardiogram in the form of inequality of intervals R-R. In order to avoid this, the operator has to select the time delay of the stimulation so that the stimulation occurs at certain delayed time point after the T wave in a cardiogram so as to prevent the occurrence of stimulation in the systole phase that would inevitably have negative or even fatal effect on a patient's health.

Obviously, the effect of therapy in this event completely depends upon the operator's expertise and diligence. In the event of arrhythmia, the problem seems even more severe that could lead to a fatal result.

Known in the art are also a method and system for external counterpulsation therapy (application US 2009/0036938) wherein the system employs muscle stimulation transducers in order to stimulate skeletal muscle and/or vascular smooth muscle in synchronization with the cardiac cycle in a manner that increases the fluid pressure within veins and/or arteries during cardiac diastole.

SUMMARY

In the aforementioned method and system, transducers of the signals of the heart electrical activity as well as of other physiologically changing signals, such as for example audio signals of the heart, are used.

In the aforementioned US patent application, it is not disclosed the differentiation of the heart sounds, specifically I and II sounds, or, optionally, III and IV sounds, in monitoring the audio signals (sounds), which is particularly necessary for patients suffering from valvular disorder of the heart, adiposis and tachyarrhythmia Among the patients of the mentioned category it is difficult to determine II (aortic) sound due to intra- and extra-cardiac noises that would enable to accurately detect the starting point of the diastolic phase, and, therefore, it is likely that the stimulation may start in the wrong phase.

Technical result of the invention is enhancing the counterpulsation therapy and, at the same time, preventing the negative effect of the therapy by application of the stimulating impulses in precisely determined time point.

The method of counterpulsation therapy according to the present invention comprises the steps of monitoring the signals of electrical and acoustic activity of the heart; precisely detecting the heart diastolic phase starting point; and stimulating the muscles; wherein, for the purposes of determination of starting moment of the diastolic phase, the R wave is determined in a cardiogram, at the time of blocking the signal of the cardiac acoustic activity; then the beginning of II (aortic) sound is determined in a phonocardiogram at the time of unblocking the signal of the cardiac acoustic activity, and, blocking the signal of the cardiac electrical activity; and in the beginning of II (aortic) sound, feeding packets of electrical impulses is initiated each packet having the duration of 7-15% of interval R-R.

Thus, in accordance with the method of the present invention, the combination of the signals of the electrical activity of the heart and acoustic signals of the heart is used in such a manner that R wave is initially determined in a cardiogram, followed by II (aortic) sound of the heart, which appears within about 300 ms after the determined R wave. The electrical impulses are acted on muscles in the moment of II sound.

It is also provided by the present invention a device of counterpulsation therapy for accomplishment of the above described method. The device comprises at least one device of stimulation of skeletal muscles and/or smooth muscles; a sensor of the cardiac electrical activity signal and a sensor of cardiac acoustic signal; a control device connected to the said sensors for controlling and actuating at least one device of stimulation of skeletal muscles and/or smooth muscles in the diastolic phase of the heart, that comprises at least one output for connecting with stimulation devices; the cardiac electrical activity signal blocking unit having one input connected with the cardiac electrical activity signal sensor, and a second input connected with the control device, and an output connected with the same control device; a second unit of blocking the acoustic signal having an input for receiving the signal from the sensor of acoustic signals, and an output connected with the control unit, and a second input for receiving the feedback signal from the control device; wherein the control device is adapted to determine, against the background of the blocked acoustic signal, the time moment that corresponds to the R wave of the signal received from the cardiac activity sensor; and to unblock the signal of the cardiac acoustic activity within 200 ms from the beginning of the time moment and block the signal of cardiac electrical activity; and then to determine the precise moment of starting II (aortic) sound by monitoring the acoustic signal so as to feed electrical impulses from the stimulation device by the signal control device.

The present invention in its one aspect provides for stimulating smooth muscles and celiac plexus in counterpulsation mode from the gastrointestinal lumen by use of a capsule (see FIG. 3) swallowed by a patient. The capsule passes the gastrointestinal tract and biologically leaves the organism in 24-48 hours.

The aforementioned capsule is a device similar to gastrointestinal tract electrical stimulator produced by NPO ECOMED (see for example the Russian patent RU 2071368 and the author's certificate of USSR SU 936931) that comprises two separated from each other electrodes and electrical supply source and impulse generator accommodated within the capsule.

The aforementioned capsule for electrical stimulation suffers from the drawback in that it operates in asynchronous mode and, therefore, it cannot perform stimulation in synchrony with cardiac operation cycle.

The capsule in accordance with the present invention can be used also for the treatment of cardiac and vascular disorders, aside from the gastrointestinal tract.

In accordance with the present invention, the aforementioned capsule is further provided with a wireless unit, such as for example a radiofrequency signal receiving unit. This unit receives the stimulation signals from one output of the control device 5 (see FIG. 1) through a radio communication channel, for example by use of a well-known BLUETOOTH standard, and performs stimulation of smooth muscles in synchrony with cardiac operation cycle, as was described above. Obviously the control unit should be provided with a radiofrequency signal transmission unit for this purposes, or such a unit has to be connected to its output.

DETAILED DESCRIPTION

Figure 1:
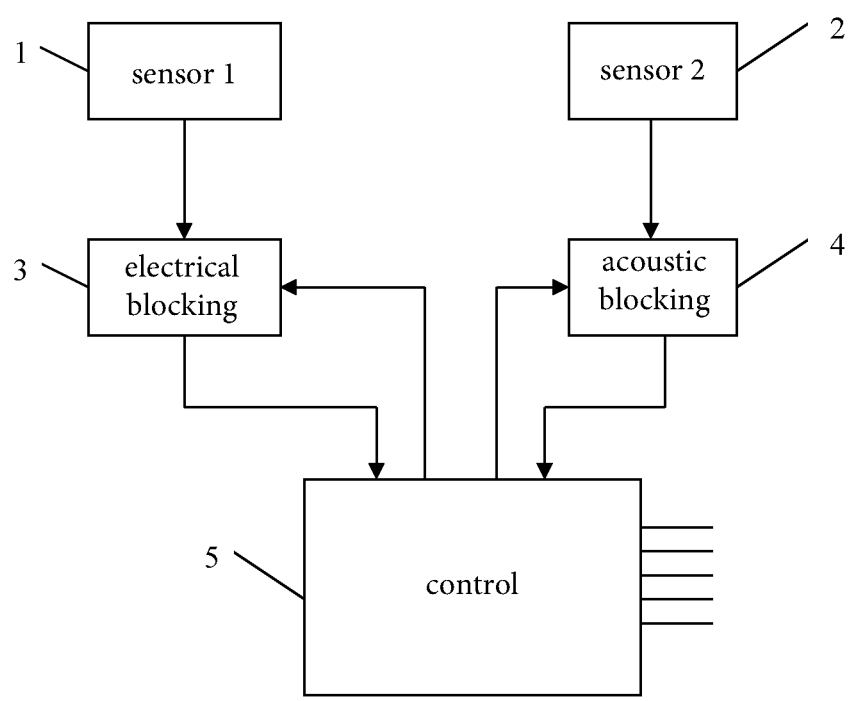
FIG. 1 illustrates the diagram of the therapy device according to the present invention.

The device comprises a sensor 1 of the cardiac electrical activity signal; a sensor 2 of cardiac acoustic signal; a unit 3 for blocking the cardiac electrical activity signal coming from the sensor 1 of the cardiac electrical activity signal; a unit 4 for blocking the acoustic signal coming from the sensor 2 of cardiac acoustic signal; a control device 5 having outputs wherefrom the signals are fed to muscle stimulating devices (not shown in the figure).

An ECG device or Polar type fitness-electrode can be used as a sensor 1 of the cardiac electrical activity signal.

The control device 5 can be a computer equipped with suitable software means or with other digital or analog device known to those skilled in the art for performing the control function.

The control device 5 can be provided with several (preferably 4) outputs for feeding the stimulation signals to, e.g., sura and femora.

Figure 2:
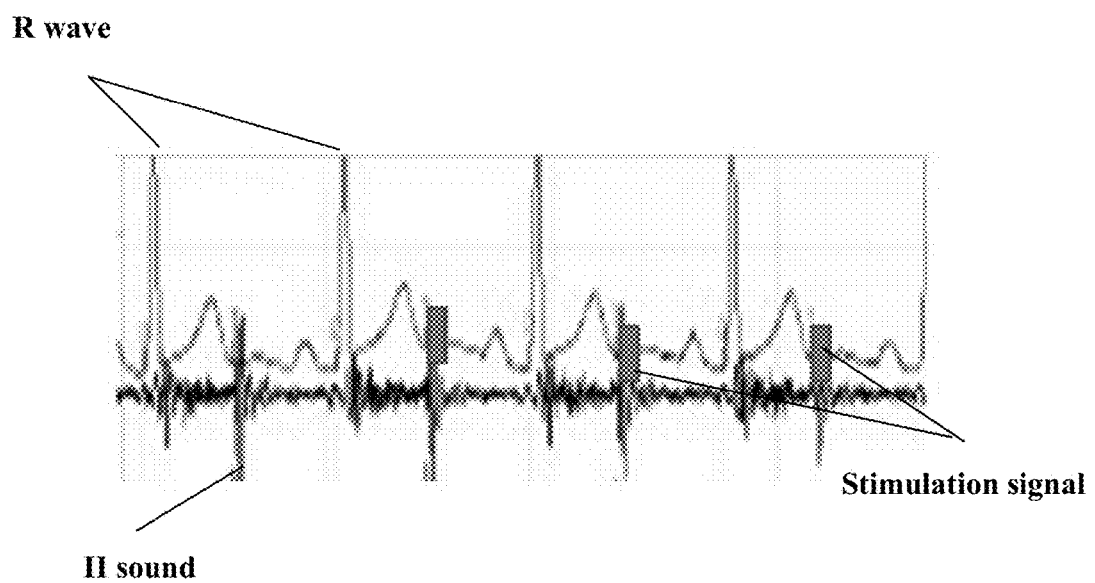
FIG. 2 illustrates curves of cardiac electrical activity and cardiac acoustic signals.
Figure 3:
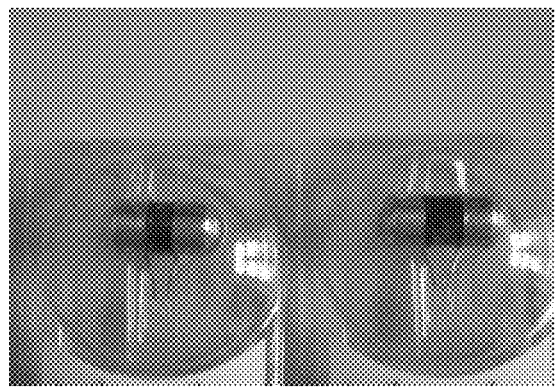
FIG. 3 illustrates the capsule for electrical stimulation of the gastrointestinal tract.

The method is performed in the following manner:

Initially R wave is determined in electrocardiogram obtained from sensor electrodes affixed to the patient's sternum (see FIG. 2). For this purposes, the signal coming from the ECG 1 (FIG. 1), which describes the cardiac electrical activity, is fed to one input of the control device 5 through the radio communication channel and blocking unit 3 (at this time the blocking is switched off). At the same time, the acoustic signal generated by the sensor 2 of the acoustic signal is blocked by the signal fed from the control device 5 output to the blocking unit 4. In approximately 200 ms from the moment of determining the R wave, acoustic signal is unblocked by the control device 5. Starting from this moment, after the certain time period, the acoustic signal sensor 2 generates the signal of II (aortic) sound corresponding to the beginning of the diastole phase, and the control device 5 at this moment block the ECG signal by feeding the blocking signal to the unit 3. At this time, the control device 5 generates the muscle stimulating signal, of which duration is 7-15% of the R-R interval. The ECG signal is kept blocked after ending the stimulation within a time of about 10 ms. Then the steps are repeated.

It is preferable to affix the acoustic sensor (microphone) in the area of projection of the aortic valve or in other area wherein the cardiac sounds are clearly expressed.

The above described method enables to automatically determine the R wave (cardiac electrical activity signal) with relatively big amplitude and II (aortic) sound (cardiac acoustic activity signal) for defining the exact moment of beginning of the stimulation and, thereby, to exclude the need in the operator's intervention and possible negative effects related with such an intervention.

Citations:
1. Patent of Georgia GE 118; IPC: A61B 17/00; published Dec. 26, 1994.
2. Patent of Georgia GE 366; IPC: A61N 1/36; published Jul. 01, 1996.
3. US patent application US 2009/0036938 A1; IPC: A61N 1/04; published Feb. 05, 2009.
4. Patent of Russia RU 2071368; IPC: A61N 1/375; published Jan. 10, 1997.

We claim:

1. A method of counterpulsation therapy comprising the steps of monitoring the signals of cardiac electrical and acoustic activities; determining the moment of beginning a diastole phase of a cardiac cycle; and stimulating muscles, wherein in order to accurately determine the moment of beginning the diastole phase of the cardiac cycle in a cardiogram, the R wave is determined at the time of blocking the signal of the cardiac acoustic activity; then the beginning of II (aortic) sound is determined in a phonocardiogram at the time of unblocking the signal of the cardiac acoustic activity, and blocking the signal of the cardiac electrical activity; and, in the beginning of II (aortic) sound, feeding packets of electrical impulses is initiated, each packet having the duration of 7-15% of R-R interval.

2. A device for counterpulsation therapy, comprising at least one device for stimulating skeletal and smooth muscles; a sensor of the signal of cardiac electrical activity and a sensor of cardiac acoustic signal; a control device connected to said sensors for actuating at least one device of stimulation of skeletal and/or smooth muscles in diastole phase of the cardiac cycle, the control device comprising at least one output for coupling with the at least one device for stimulating, wherein it further comprises a unit for blocking the cardiac electrical activity signal, the unit having one input connected with said sensor of the signal of cardiac electrical activity, and a second input connected with the control device, and an output connected with the control device; a second unit for blocking the acoustic signal, the unit having an input through which the signal from said sensor of acoustic signals is fed, and an output connected with said control device, the signal from the control device being in turn fed by feedback to a second input; wherein said control device is adapted to determine, while the acoustic signal is blocked, the time point corresponding to the R wave on the signal received from said sensor of the signal of cardiac electrical activity; to unblock the signal of the cardiac acoustic activity within the time period of about 200 ms from the beginning of this time point and to block the signal of the cardiac electrical activity; and, further, to determine the exact moment of beginning II (aortic) sound by monitoring the acoustic signal in order to feed electrical impulses by the control device to the stimulation devices.

3. A device for counterpulsation therapy in accordance with claim 2, wherein said stimulation device has the shape of an orally administered capsule and is connected with said control device by means of a wireless communication.

* * * * *